United States Patent
Pudleiner et al.

[11] Patent Number: 5,942,593
[45] Date of Patent: Aug. 24, 1999

[54] CYCLOALIPHATIC THERMOPLASTIC POLYURETHANE ELASTOMERS

[75] Inventors: Heinz Pudleiner; Rolf Dhein, both of Krefeld; Herbert Hugl, Bergisch Gladbach; Hanns-Peter Müller, Odenthal; Herbert Heidingsfeld, Frechen; Hans-Georg Hoppe, Leichlingen, all of Germany

[73] Assignee: Bayer Aktiengesellschaft, Leverkusen, Germany

[21] Appl. No.: 08/805,840

[22] Filed: Mar. 3, 1997

Related U.S. Application Data

[63] Continuation of application No. 08/510,528, Aug. 2, 1995, abandoned.

[30] Foreign Application Priority Data

Aug. 11, 1994 [DE] Germany ............................ 44 28 458

[51] Int. Cl.$^6$ ................................................. C08G 18/44
[52] U.S. Cl. .................................. 528/49; 528/64; 528/67
[58] Field of Search ................................... 528/49, 64, 67

[56] References Cited

U.S. PATENT DOCUMENTS

| | | | |
|---|---|---|---|
| 3,849,360 | 11/1974 | Farah et al. | 260/33.2 R |
| 4,041,208 | 8/1977 | Seeger | 428/424 |
| 4,062,834 | 12/1977 | Gilding et al. | 260/75.5 AA |
| 4,303,773 | 12/1981 | Ganster et al. | 528/64 |
| 4,342,847 | 8/1982 | Goyert et al. | 525/66 |
| 4,521,582 | 6/1985 | Goyert et al. | 528/67 |
| 4,574,147 | 3/1986 | Meckel | 528/64 |
| 4,948,860 | 8/1990 | Solomon et al. | 528/28 |
| 5,373,068 | 12/1994 | Piana et al. | 525/403 |
| 5,436,399 | 7/1995 | Koyama et al. | 528/59 |

FOREIGN PATENT DOCUMENTS

| | | |
|---|---|---|
| 12343 | 6/1980 | European Pat. Off. . |
| 282771 | 9/1988 | European Pat. Off. . |
| 604890 | 7/1994 | European Pat. Off. . |
| 1339813 | 12/1973 | United Kingdom . |
| 1508317 | 4/1978 | United Kingdom . |

OTHER PUBLICATIONS

Chemical Abstracts, vol. 101, No. 26, Dec. 1984, Abstract No. 232028x 'Polyurethane Solutions', p. 72 and JP–A–59 108 021 (Sanyo).
Journal of Applies Polymer Science, Bd. 51, Nr. 1, Jan. 3, 1994, pp. 43–49, Ahn et al 'The Properties of Polyurethane with Mixed Chain Extenders and Mixed Soft Segments'.
D.J. Williams; Polymer Science & Engineering; 1971, p. 55.
F.M. Sweeney; Introduction to Reaction Injection Molding; 1979; p. 50.

Primary Examiner—Rachel Gorr
Attorney, Agent, or Firm—Joseph C. Gil; Aron Preis

[57] ABSTRACT

A process for the preparation of a polyurethane-urea elastomer having a mole ratio of NCO groups to all active hydrogen atoms in the range of 0.9 to 1.2 is disclosed. The process comprise reacting (A), (B) and (C.2) for form an NCO-containing prepolymer and then reacting said prepolymer with (C.1) and (D). Accordingly (A) is 5-isocyanato-1-(isocyanatomethyl)-1,1,3-trimethylcyclohexane or bis-(4-isocyanatocyclohexyl)-methane,(B) is polytetrahydrofuran or hexanediol polycarbonate and (C.2) is a chain extender. (C.1) is 5-amino-3-amino-methyl-1,3,3-trimethylcyclohexane or bis-(4-aminocyclohexyl)-methane and (D) is a molecular weight regulator. The elastomer thus produced is particularly suitable for the preparation of moldings, films, flexible tubing (for medical purposes) and catheters.

25 Claims, No Drawings

CYCLOALIPHATIC THERMOPLASTIC POLYURETHANE ELASTOMERS

This application is a continuation, of application Ser. No. 08/510,528 filed Aug. 2, 1995, now abandoned.

Polyurethane elastomers are produced from three basic components: a polyisocyanate, a macrodiol, and a chain extender which is generally a low molecular weight diol, diamine or amino alcohol, or water. If a diol is used as the chain extender, the polyurethane formed exclusively contains urethane bonds, apart from allophanate or biuret groups formed by secondary reactions. If water, amino alcohols or diamines are used, both urethane and urea groups are formed and the product is described as polyurethane-urea.

Polyurethane elastomers are $(AB)_n$ block copolymers, and due to the more or less strongly pronounced incompatibility of their polymer blocks they form micro-domains which are termed hard and soft segments. The hard segment (block A) is formed from the polymer regions which are produced by the reaction of the isocyanate component with the chain extender. In general, this segment exhibits a high degree of crystallinity and is mainly responsible for the mechanical and thermal properties, i.e. the melting behavior during forming processes. The melting temperature of the hard segment must be higher than the temperature of use. The soft segment (block B) is formed from the polyether or polyester fractions of the polymer chain and is generally amorphous or only slightly crystalline; its glass transition temperature must be far below the temperature of use.

Polyurethane elastomers attain their thermoplastic character in that the hard segments melt at high temperatures, so that a decrease of the viscosity and the formation of a melt occur. On cooling, e.g. in the water bath downstream of an extruder, the hard segments crystallize and the solid, elastomeric molding is produced.

The present invention relates to polyurethane elastomers obtained from

A) 5-isocyanato-1-(isocyanatomethyl)-1,1,3-trimethylcyclohexane (isophorone diisocyanate) and/or bis-(4-isocyanatocyclohexyl)-methane and B) polytetrahydrofuran and/or hexanediol polycarbonate with molecular weights of 1500 to 3000 in the mole ratio A):B)=1.2:1 to 30:1, C) a chain extender mixture comprising
   C.1) 5-amino-3-aminomethyl-1,3,3-trimethylcyclohexane (isophoronediamine) and/or bis-(4-aminocyclohexyl)-methane and
   C.2) 1,6-hexanediol, 1,4-butanediol, diethylene glycol, di- and tripropylene glycol and/or hydroquinone di-β-hydroxyethyl ether, in the mole ratio C.1):C.2)= 60:40 to 20:80, and D) 0.01 to 7 equivalent %, based on the NCO groups in A), of a monoisocyanate, monoalcohol or monoamine (as a molecular weight regulator), wherein A), B) and C.2) are reacted in a first stage to form an NCO prepolymer, and the latter is reacted with C.1) and D) in a second stage to form the polyurethane-urea, and wherein the mole ratio of NCO groups to all the active hydrogen atoms is 0.9:1 to 1.2:1.

The invention also relates to moldings, particularly films, flexible tubing (for medical purposes) and catheters made of these polyurethane elastomers, and to the use of the polyurethane elastomers for the production of these moldings.

Polyurethanes which have been extended by diols, for use as a material for flexible tubing and catheters, are known by the trade names Pellethane® (Dow Chemical Co.) and Tecoflex® (Thermedics Inc.). These products are generally manufactured by the "one-shot" process, in which all the components are mixed in the melt and then react with each other, or by the two-stage "prepolymer" process, in which a prepolymer is first formed from the macrodiol and the isocyanate component and is then reacted in a second stage with the chain extender to form the polyurethane. These products exhibit good biocompatibility, but necessitate the addition of a heavy metal catalyst, e.g. dibutyltin dilaurate, particularly for the reaction of the hydroxyl groups with the isocyanate groups. Such catalysts are inherently toxic to cells and if at all possible should not be present in material for use in the body.

In particular, the reaction of cycloaliphatic polyisocyanates with glycols proceeds relatively slowly, even at temperatures between 150° C. and 180° C., so that, in order to increase the rate of reaction, catalysis, generally by heavy metal compounds, cannot usually be dispensed with. Moreover, with the softer (Shore A 70 to 85) product compositions comprising aliphatic thermoplastic polyurethanes based on a mixture of bis-(4-isocyanatocyclohexyl)-methane isomers, a problem arises during processing in that the moldings produced still exhibit pronounced surface tackiness, particularly directly after processing. This unwanted property necessitates special processing techniques in which the individually produced parts do not contact each other, at least until this effect has diminished due to the completion of crystallization of the hard segments.

In contrast, the reaction of amines with isocyanates offers certain advantages: it generally requires no external catalysis; the reaction of primary aliphatic amines with isocyanates proceeds so rapidly, even at room temperature, that it is no longer possible to carry out the reaction homogeneously in the melt due to the immediate precipitation of urea. The urea groups which are formed form hard segments which exhibit improved crystallization behavior, so that surface tackiness does not have to be taken into account.

Polyurethaneureas per se have already been known for a long time. However it has not been possible to produce high molecular weight, elastomeric polyurethane-ureas in their undiluted state from polyisocyanates, macrodiols and polyamines by the usual methods described above, because the reaction between aliphatic amino groups and isocyanate groups proceeds so energetically that a homogeneous mixture of the reactants is no longer possible before solidification of the reaction product occurs. Hitherto, polyureas of this type have therefore always been produced in highly dilute solution. This means that either a large amount of solvent has to be removed from the production stage, or an additional evaporation step, which is costly on an industrial scale, has to be disposed downstream of the polyurethane-urea production stage, and that when coating a medical article, such as a catheter for example, it must be ensured in particular that the coating is dried free from solvent An aromatic polyurethane-urea is offered as a solution for medical use under the trade name Biomer® (Ethicon Corp.).

The melting range of normal polyurethane-ureas such as these is generally above their decomposition temperature, so that products such as these are unsuitable for thermoplastic processing.

U.S. Pat. No. 4,062,834 disclosed a method of producing a purely aromatic thermoplastic polyetherurethane-urea, in which the polymer is produced in solution, using water as the chain extender, and subsequently has to be precipitated and worked up in a manner which is expensive on an industrial scale. It is clear from the mechanical property data given that the products produced by this method have tensile strengths which are considerably lower, for example, than those of polyurethane-ureas, the chains of which are extended solely using diamines. It is clear from the molecular weight data given in the above patent that thermoplasticity was obtained at the expense of a high molecular weight.

DE-OS 2,423,764 discloses a process for producing polyurethane-ureas by the reaction of polyisocyanates, macrodiols and polyamines in the melt by the reaction extrusion method. The thermoplastic processability of the products produced in this manner is also mentioned in this Application, but these polymers do not by any means attain the excellent melting and processing behavior of the polyurethane-ureas according to the present invention, which is comparable with that of customary polyurethanes. Moreover, the use of such products for catheter and flexible tubing applications is not mentioned.

Polyurethane-urea copolymers which can be processed from the melt, and a process for producing them, are disclosed in EP 0,396,270. Amongst other measures, an essential part of the invention disclosed therein is the setting of an NCO/OH or NCO/NH ratio which is preferably 120. However, as our comparative tests have shown, this results in polyurethane-ureas which exhibit melting behavior which is considerably inferior to that of polyurethanes. In addition, it is stated therein that subsequent "post curing" is always necessary for the polyurethane-ureas produced by all the process variants of EP 0,396,270.

In contrast, the polyurethane elastomers according to the present invention have the following advantages:

melt volume index at 190° C./5 kg of 1 to 200 cm$^3$/10 minutes, transparency, improved compatibility with cells, melt viscosities and flowabilities like those of pure thermoplastic polyurethanes, capable of being processed in standard machines without the products sticking together, capable of being produced in reaction extruders, improved quality of extrusion, production without solvents and without catalysts.

5-isocyanato-1-(isocyanatomethyl)-1,1,3-trimethylcyclohexane (isophorone diisocyanate) (preferably about 70 weight % of the cis isomer and about 30 weight % of the trans isomer) and/or 4,4'-bis-(isocyanatocyclohexyl) methane with preferably 20 to 95 weight of a trans,trans-isomer content, is used as component A) for the production of the polyurethane elastomers according to the invention.

Polytetrahydrofuran (polytetrahydofurandiol) and/or hexanediol polycarbonate with number average molecular weights of 1500 to 3000 must be used as the higher molecular weight polyhydroxy compound B). It has proved to be particularly advantageous to use polytetrahydrofuran with an average molecular weight of about 1750 to 2500 as component B).

In contrast, polytetrahydrofuran with an average molecular weight of 1000 produced tacky products which could not be processed further.

Mixtures of 99 to 1 weight % polytetramethylene glycol ether with 1 to 99 weight % hexanediol polycarbonate may also be used as component B). However, these generally have an unfavorable effect on the tackiness, so that this form of the process is not preferred.

The mole ratio of component A) to component B) is 1.2:1 to 30:1, preferably 1.5:1 to 20:1. Ratios of 2:1 to 12:1 are particularly preferred. Products of this type result in elastomers with hardnesses from 80 Shore A to 80 Shore D. Those with hardnesses from 85 Shore A to 70 Shore D are preferred.

Suitable chain extender mixtures C) are those containing cycloaliphatic diamines, preferably containing isophoronediamine and/or bis-(4-aminocyclohexyl)-methane as component C.1) and one or more (e.g. two or three) further diols C.2) with a molecular weight of 62 to 399, preferably 1,4-butanediol, 1,6-hexanediol, diethylene glycol, dipropylene glycol, tripropylene glycol and hydroquinone-di-β-hydroxyethyl ether, most preferably 1,6-hexanediol. A mixture of 60 to 20 mole % isophoronediamine and 40 to 80 mole % 1,6-hexanediol is preferred; a mole ratio from 50 to 30 mole % to 50 to 70 mole % is particularly preferred.

In addition, monofunctional compounds D) (molecular weight regulators) are used conjointly in the form known to one skilled in the art. Examples include monohydric alcohols such as butanol, ethyl hexanol, isobutyl alcohol, 1-octanol or stearyl alcohol; diamines such as dibutylamine, N-methylstearamine or piperidine; or monoisocyanates such as stearyl isocyanate. Dibutylamine is preferred.

Component D) must be used in amounts of 0.01 to 7 equivalent %, preferably 2 to 6 equivalent %, based on the content of NCO groups of component A). The optimum processing properties are only attained for the polymers if a content of 2 to 6 equivalent %, based on component A), is used, which is relatively high for chain regulators. Moreover, despite the comparatively high content of molecular weight regulator it has surprisingly been found that products are obtained which are free from tackiness and which can satisfactorily be processed further, and which exhibit excellent mechanical and thermal properties.

Preferably 0.1 to 3 weight % (based on the total amount of the other components) of waxes, antioxidants and/or UV absorbers may be used conjointly as component E). Mixtures of stabilizers are preferably used. Only the minimum amounts of such additives should be used—if they are used at all—so that the compatibility with cells is not impaired.

The antioxidants which may be used comprise all products which are known for this purpose, such as those described in EP-A 12,343 for example. Antioxidants based on sterically hindered phenols are preferred, such as 2,6-di-t-butyl-4-methylphenol and pentaerythrityl tetrakis-3-(3,5-i-t-butyl-4-hydroxyphenyl)-propionate (Irganox® 1010, Ciba-Geigy), for example.

The usual catalysts, mold release agents, antistatic agents, flame retardants, fillers and colorants may be added during the production of the polyurethane elastomers (see DE-OS 2,854,409, DE-OS 2,920,501 and DE-P 3,329,775, for example). The aforementioned additives are preferably omitted, however, particularly if the elastomers are to be used for medical purposes; the exceptions are special fillers, such as barium sulphate or bismuth oxide, for example, for the production of mixtures capable of exhibiting a high contrast with X-rays, and mold release agents for obtaining particularly smooth surfaces.

Examples of catalysts which can be used include tertiary amines, organic metal compounds, particularly organic tin, lead and titanium compounds, e.g. tin(II) acetate, tin(II) ethylhexanoate, dibutyftin laurate or lead acetate. Preferably, no catalyst is employed.

Waxes or oils may be used as mold release agents. Other examples of mold release agents include long chain compounds containing carboxyl, ester, amide, urethane or urea groups, such as those listed in DE-OS 2,204,270, for example. Bis-ethylene stearylamide is preferred.

The amounts of reaction components A) to C) are selected for the polyurethane elastomers according to the invention so that the NCO/OH or NCO/NHR ratio of isocyanates to OH compounds or amine compounds is between 0.9 and 1.2, preferably between 0.98 and 1.05, most preferably 1:1.

The polyurethane-ureas according to the invention are preferably produced continuously or batch-wise by a two-stage process, wherein components A) and B) and the aliphatic dihydroxy compounds of component C) are most preferably reacted to form an NCO-containing prepolymer, and the prepolymer is then dissolved in a suitable organic solvent, e.g. toluene, and its chain length is extended using the cycloaliphatic diamine of component C) dissolved in toluenelisopropanol, for example. However, a chain extension process is preferred in which the prepolymer is added in metered amounts as a melt to the reaction screw feeder, together with metered amounts of the monofunctional compound (component D) and the cycloaliphatic diamine of component C), and these materials are reacted there to form the final thermoplastic polyurethane elastomer. In contrast to EP-A 0,396,270, in this production process the final, completely reacted polyurethane elastomer is obtained, which no longer has to be post-cured in a further process step by storage in moist or normal ambient air, as described in EP-A 0,396,270.

The polyurethane elastomers according to the invention exhibit very good compatibility with cells, as can be seen from the data of Table 1. The ability to produce the polyurethanes free from catalysts is advantageous in this respect.

In the cell compatibility tests, L cells were cultured and then cultured further in the presence of a sample to be tested or an aqueous extract of the latter. Amongst the various parameters evaluated on the completion of the tests, the evaluation of the DNA and protein synthesis capacity demonstrated the advantages of the polyurethane-urea samples particularly clearly.

Methods of determination

TABLE 1

Compatibility of elastomer-urea from Example 2 with cells, compared with that of the comparison examples

|  | Comparison Example 1 | Comparison Example 2 | Comparison Example 3 | Polyurethane-urea (Example 2 |
|---|---|---|---|---|
| DNA synthesis yield relative to the control | 35% | 50% | 62% | 61% |
| Protein synthesis yield relative to the control | 65% | 70% | 82% | 78% |

Comparison Example 1: a commercially available aliphatic thermoplastic polyurethane for medical applications, of hardness 85 Shore A.
Comparison Example 2: a commercially available aliphatic thermoplastic polyurethane for medical applications, of hardness 93 Shore A.
Comparison Example 3: a commercially available aliphatic thermoplastic polyurethane for medical applications, of hardness 60 Shore D.
Example 2: polyetherurethane-urea (see the Examples) (92 Shore A).

In these tests, only materials of the same hardness should be compared with each other. Table 1 shows that the polyetherurethane-urea is considerably better than the material of comparable hardness, and is almost as good as the polyurethane which is significantly harder.

Tests for determining the time-dependence of surface tackiness

Several samples of the material to be tested, which all had the same surface area, were each annealed for 10 minutes at 150° C. All the samples were removed simultaneously from the annealing oven (time of measurement t=0) and kept at room temperature until measurements were made. Two test faces of the same material in each case were then pressed together in a measuring apparatus under the same contact pressure and for the same time of pressing, and the force required to separate the samples was determined at the same rate of pull-off. Measurements were made on the samples 2, 3, 4, 5 and 6 minutes after annealing in each case.

TABLE 2

Surface tackiness [N/mm]

|  | 2 min | 3 min | 4 min | 5 min | 6 min |
|---|---|---|---|---|---|
| Comparison Example 3 | 0.90 | 0.60 | 0.5 | 0.2 | 0.1 |
| Comparison Example 1 | 0.95 | 0.95 | 0.9 | 0.85 | 0.4 |
| Example 2 | 0.2 | 0.2 | 0.15 | 0.12 | 0.1 |
| Example 8 | 0.5 | 0.45 | 0.35 | 0.25 | 0.2 |

For the product from Example 2 the surface tackiness clearly decreased earlier than for the products from the comparison examples. It was also verified that the product with the soft segment comprising polytetrahydrofuran (PTHF) of molecular weight 2000 was less tacky than that containing PTHF of molecular weight 1000.

A major advantage of the thermoplastic polyurethane-ureas according to the invention is manifested in that they combine excellent mechanical, optical and toxicological properties with the possibility of thermoplastic processability, free from tackiness, by injection molding or extrusion. As shown in Table 3, the polyurethanes according to the invention behave as regards their temperature dependent melt flow index (MVI=melt volume index) like thermoplastic polyurethanes which are free from urea groups.

TABLE 3

Melt volume indices
Conditions of measurement: DIN ISO 1133
Melt volume index (MVI)

|  | MVI (190° C./5 kg)/cm³/10 min | MVI (200° C./5 kg)/cm³/10 min |
|---|---|---|
| Example 1 | 32.14 | 65.03 |
| Example 2 | 2.98 | 8.4 |
| Comparison Example 4 | 4.46 | 12.59 |
| Comparison Example 1 | 29.29 | 126.28 |
| Comparison Example 5 | 0.06 | 0.44 |
| Comparison Example 6 | 0.01 | 1.22 |
| Comparison Example 7 | 0.2 | 1.4 |
| Example 3 | 4.41 | 18.95 |
| Example 4 | 152.6 | 392 |
| Example 5 | 11.45 | 29.32 |
| Example 6 | 2.37 | 6.5 |
| Example 7 | 1.01 | 3.37 |

The polyurethane-ureas according to the invention have also been proven in practice to have a good capacity for processing. It was possible to produce transparent catheter tubing and blown film tubing free from pinholes in an extrusion process.

It can be seen from Table 4 that the melting of the polyetherurethane-urea from Example 2 for catheters in a Brabender PL 2000 measuring extruder at constant temperature (198° C.) and rotational speed (19 rpm) resulted in a uniform torque and a constant melt pressure over the period of measurement. These data verify that the polyurethane-urea is suitable for attaining a stable processing operation, and unwanted additional curing reactions downstream of the actual polymer-forming reaction on the machine do not occur.

TABLE 4

Time dependence of the extrusion process parameters - data based on processing of material of Example 2.

| Time (min) | Torque (NM) | Pressure (bar) |
|---|---|---|
| 0 | 119.5 | 48 |
| 1 | 124.7 | 51 |
| 2 | 124.8 | 52 |
| 3 | 125.3 | 52 |
| 4 | 125.8 | 52 |
| 5 | 125.8 | 51 |
| 6 | 125.5 | 52 |
| 7 | 125 | 52 |
| 8 | 125.8 | 52 |
| 9 | 126.4 | 52 |
| 10 | 122.9 | 51 |
| 11 | 123.7 | 52 |
| 12 | 122.8 | 51 |
| 13 | 124.4 | 51 |
| 14 | 125.7 | 50 |
| 15 | 122.8 | 50 |
| 16 | 124.9 | 50 |
| 17 | 124.7 | 50 |
| 18 | 124.4 | 50 |
| 19 | 121.7 | 50 |
| 20 | 123.7 | 51 |

The invention is further illustrated but is not intended to be limited by the following examples in which all parts and percentages are by weight unless otherwise specified.

EXAMPLES

Example 1

720 parts of polytetrahydrofuran (Terathane 2000®) and 76.6 parts of 1,6-hexanediol were dehydrated for 1 hour at 120° C. under the vacuum from a water pump in a flask with a surface-ground seal, fitted with a stirrer and an internal thermometer (water content<0.04 weight %). 329.8 parts of 5-isocyanato-1-isocyanatomethyl)-1,1,3-trimethylcyclohexane (isophorone diisocyanate) were added, and the mixture was stirred for 3 hours at 120° C. until the theoretical NCO number of 3.5 weight % was attained (measured: 3.55 weight %).

12 parts of ethylene bis-stearylamide and 15.3 parts of di-n-butylamine were then added. This prepolymer was dissolved in 634 parts of toluene and was added drop-wise with stirring at room temperature to a solution of 73.6 parts of 5-amino-3-aminomethyl-1,3,3-trimethylcyclohexane in 2990 parts of toluene/isopropanol (70:30). A colorless, transparent, homogeneous solution of the polyurethane-urea was obtained, which gave a transparent, colorless, non-tacky film after drying. After injection molding the chopped films, a tensile strength of 45.5 MPa and an elongation at tear of 560% were measured on injection molded test specimens.

Example 2

This example illustrates the preferred production of the polyurethane-ureas.

A prepolymer containing 3.5% of free isocyanate groups was prepared from 587 parts of anhydrous polytetrahydrofuran (Terathane 2000®) of average molecular weight 2000, 62.5 parts of 1,6-hexanediol and 269 parts of 1-isocyanato-3-isocyanatomethyl-3,5,5-trimethylcyclohexane (isophorone diisocyanate), at 120° C. under nitrogen and with stirring, over the course of 3 hours, and was mixed with 9.8 parts of ethylene bis-stearylamide wax. The resulting prepolymer was held under nitrogen at 80° C.

1700 parts per minute of the product held under nitrogen at 80° C. were added, from a heated vessel via a gear pump, together with 110 parts per minute of 5-amino-3-aminomethyl-1,3,3-trimethylcyclohexane from a second vessel maintained at 80° C., and 11 parts per minute of di-n-butylamine from a third vessel maintained at 30° C., to the inlet connection piece of a double-shaft screw machine, the shafts of which were rotating at 200 rpm in the same direction (a double-shaft, unidirectionally rotating, self-cleaning screw machine Type ZDSK 53, manufactured by Werner & Pfleiderer). Approximate product temperatures of about 145–235° C. were measured over the length of the machine. The lowest temperatures were determined on or just in front of the perforated outlet nozzle plate. The product emerging from the machine was cooled in a water bath and comminuted in a granulator. The granulated material was non-tacky and completely transparent, and was subsequently dried at 70° C. After injection molding, a tensile strength of 39.9 MPa and an elongation at tear of 556% were measured on injection molded test specimens.

Example 3

The prepolymer was prepared at 120° C. from 480 parts of polytetrahydrofuran (Terathane 2000®), 128.15 parts of 1,6-hexanediol and 468.77 parts of 5-isocyanato-1-isocyanatomethyl)-1,1,3-trimethylcyclohexane (isophorone diisocyanate), as described in Example 1.

12 parts of ethylene bis-stearylamide and 21.8 parts of di-n-butylamine were then added. This prepolymer was dissolved in 634 parts of toluene and was added drop-wise with stirring at room temperature to a solution of 123.08 parts of 5-amino-3-aminomethyl-1,3,3-trimethylcyclohexane in 2990 parts of toluene/isopropanol (70:30). A colorless, transparent, homogeneous solution of the polyurethane-urea was obtained, which gave a transparent, colorless, non-tacky film after drying. After injection molding the chopped films, a tensile strength of 34.5 MPa and an elongation at tear of 395% were measured on injection molded test specimens.

Example 4

The prepolymer was prepared at 120° C. from 780 parts of polytetrahydrofuran (Terathane 2000®), 63.74 parts of 1,6-hexanediol and 295.04 parts of 5-isocyanato-1-isocyanatomethyl)-1,1,3-trimethylcyclohexane (isophorone diisocyanate), as described in Example 1.

12 parts of ethylene bis-stearylamide and 13.74 parts of di-n-butylamine were then added. This prepolymer was dissolved in 634 parts of toluene and was added drop-wise with stirring at room temperature to a solution of 61.22 parts of 5-amino-3-aminomethyl-1,3,3-trimethylcyclohexane in 2990 parts of toluene/isopropanol (70:30). A colorless, transparent, homogeneous solution of the polyurethane-urea was obtained, which gave a transparent, colorless, non-tacky film after drying. After injection molding the chopped films, a tensile strength of 31.2 MPa and an elongation at tear of 650% were measured on injection molded test specimens.

Example 5

The prepolymer was prepared at 120° C. from 720 parts of hexanediol polycarbonate (Desmophen 2020®), 76.93 parts of 1,6-hexanediol and 329.12 parts of 5-isocyanato-1-(isocyanatomethyl)-1,1,3-trimethylcyclohexane (isophorone diisocyanate), as described in Example 1.

12 parts of ethylene bis-stearylamide and 15.42 parts of di-n-butylamine were then added. This prepolymer was dissolved in 634 parts of toluene and was added drop-wise with stirring at room temperature to a solution of 72.49 parts of 5-amino-3-aminomethyl-1,3,3-trimethylcyclohexane in 2990 parts of toluene/isopropanol (70:30). A colorless, transparent, homogeneous solution of the polyurethane-urea was obtained, which gave a transparent, colorless, non-tacky film after drying. After injection molding the chopped films, a tensile strength of 53.1 MPa and an elongation at tear of 440% were measured on injection molded test specimens.

Example 6

The prepolymer was prepared at 120° C. from 720 parts of hexanediol polycarbonate (Desmophen 2020®), 66.67 parts of 1,6-hexanediol and 349.32 parts of bis-(4-isocyanato-cyclohexyl)-methane (Desmodur W®), as described in Example 1.

12 parts of ethylene bis-stearylamide and 13.79 parts of di-n-butylamine were then added. This prepolymer was dissolved in 634 parts of toluene and was added drop-wise with stirring at room temperature to a solution of 64.02 parts of 5-amino-3-aminomethyl-1,3,3-trimethylcyclohexane in 2990 parts of toluene/isopropanol (70:30). A colorless, transparent, homogeneous solution of the polyurethane-urea was obtained, which gave a transparent, colorless, non-tacky film after drying. After injection molding the chopped films, a tensile strength of 45.4 MPa and an elongation at tear of 425% were measured on injection molded test specimens.

Example 7

The prepolymer was prepared at 120° C. from 720 parts of hexanediol polycarbonate (Desmophen 2020®), 64.15 parts of 1,6-hexanediol and 339.75 parts of bis-(4-isocyanato-cyclohexyl)-methane (Desmodur W®), as described in Example 1.

12 parts of ethylene bis-stearylamide and 13.41 parts of di-n-butylamine were then added. This prepolymer was dissolved in 1000 parts of toluene and was added drop-wise with stirring at room temperature to a solution of 76.11 parts of 4,4'-bis-(aminocyclohexyl)-methane in 2624 parts of toluene/isopropanol (70:30). A colorless, transparent, homogeneous solution of the polyurethane-urea was obtained, which gave a transparent, colorless, non-tacky film after drying. After injection molding the chopped films, a tensile strength of 45.8 MPa and an elongation at tear of 405% were measured on injection molded test specimens.

Example 8 (not according to the invention)

The prepolymer was prepared at 120° C. from 720 parts of poly-tetrahydrofuran 1000 (Terathane 1000®), 60.76 parts of 1,6-hexanediol and 360.88 parts of 5-isocyanato-1-isocyanatomethyl)-1,1.3-trimethylcyclohexane (isophorone diisocyanate), as described in Example 1.

12 parts of ethylene bis-stearylamide and 16.77 parts of di-n-butylamine were then added. This prepolymer was dissolved in 634 parts of toluene and was added drop-wise with stirring at rooms temperature to a solution of 58.35 parts of 5-amino-3-aminomethyl-1,3,3-trimethylcyclohexane in 2990 parts of toluene/isopropanol (70:30). A colorless, transparent, homogeneous solution of the polyurethane-urea was obtained, which gave a transparent, colorless film after drying, which was very tacky however. After injection molding the chopped films, a tensile strength of 45 MPa and an elongation at tear of 480% were measured on injection molded test specimens.

Comparison Examples

Comparison Example 1

A commercially available aliphatic thermoplastic polyurethane for medical applications, with a hardness of 85 Shore A Comparison Example 2

A commercially available aliphatic thermoplastic polyurethane for medical applications, with a hardness of 93 Shore A Comparison Example 3

A commercially available aliphatic thermoplastic polyurethane for medical applications, with a hardness of 60 Shore D.

Comparison Example 4

A commercially available aromatic thermoplastic polyurethane for medical applications, with a hardness of 85 Shore A Comparison Example 5 (corresponding to EP 0 396 270, 70 weight % soft segment)

350 parts of polytetrahydrofuran, 12.48 parts of 1,4-butanol and 12.58 parts of 1,5-diamino-2-methylpentane (Dytek A® manufactured by Du Pont, Wilmington) were mixed at room temperature. 124.8 parts of molten 4,4'-bis-(isocyanatophenyl)-methane (MDI) at 40° C. were rapidly added, and intensive mixing was effected for two minutes by means of a stirrer. The melt was poured on to a Teflon sheet, and post-cured for 1 hour at 125° C. and then in mpist air. The polymer mat was comminuted and the MVI of the granular material was measured (see Table 3).

Comparison Example 6 (corresponding to EP 0,396,270, 60 weight % soft segment)

360 parts of polytetrahydrofuran, 23.5 parts of 1,4-butanol and 23.5 parts of 1,5-diamino-2-methylpentane (Dytek A® manufactured by Du Pont, Wilmington) were mixed at room temperature. 193 parts of molten 4,4'-bis-(isocyanatophenyl)-methane (MDI) at 40° C. were rapidly added, and intensive mixing was effected for two minutes by means of a stirrer. The melt was poured on to a Teflon sheet, and post-cured for 1 hour at 125° C. and then in moist air. The polymer mat was comminuted and the MVI of the granular material was measured (see Table 3).

Comparison Example 7 (corresponding to EP 0,348,105)

25 71.4 parts of polytetrahydrofuran 1000 (Terathane 1000®, from Du Pont, Wilmington) and 214.3 parts of polyethylene glycol 1000 were mixed and dehydrated at 120° C. under the vacuum from a water pump. 117.9 parts of 4,4'-bis-(isocyanatophenyl)-methane (MDI) at 40° C. were added under nitrogen, with intensive stirring. The mixture was stirred for 1 to 1.5 hours at 60 to 65° C. The prepolymer was then dissolved in 857.6 parts of N,N-dimethylacetamide (DMAC). 4.34 parts of ethanolamine, 4.27 parts of ethylenediamine and 0.82 parts of dimethyl ethylenediamine were dissolved in 350 parts of DMAC and rapidly added to the prepolymer solution with intensive stirring. The reaction solution was stirred for 3 hours at 85° C. A slightly yellow, viscous solution was obtained, which was dried to form a film. The dried film was comminuted and the MVI of the granular material was measured (see Table 3).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a polyurethane-urea elastomer having a mole ratio of NCO groups to all active hydrogen atoms in the range of 0.98 to 1.05, comprising reacting (A), (B) and (C.2) to form an NCO-containing prepolymer and then reacting said prepolymer with (C.1) and (D) where (A) is at least one member selected from the group consisting of 5-isocyanato-1-(isocyanatomethyl)-1,1,3-trimethylcyclo-hexane and bis-(4-isocyanatocyclohexyl)-methane and where B) is at least one member having a number average molecular weight of 1500 to 3000 selected from the group consisting of polytetrahydrofuran and hexanediol polycarbonate, and where the molar ratio (A):(B) is about 1.2:1 to 30:1, and where (C.2) is at least one member selected from the group consisting of 1,6-hexanediol, 1,4-butanediol, diethylene glycol, dipropylene glycol, tripropylene glycol and hydroquinone di-β-hydroxyethyl ether, and (C.1) is at least one member selected from the group consisting of 5-amino-3-aminomethyl-1,3,3-trimethylcyclohexane and bis-(4-amino-cyclohexyl)-methane and where the mole ratio (C.1):(C.2) is about 60:40 to 20:80, and where (D) is at least one molecular weight regulator selected from the group consisting of monoisocyanate, monoalcohol and monoamine present in an amount of 0.01 to 7 equivalent %, based on the NCO groups included in (A), said process excluding a curing step, said elastomer characterized in having a melt volume index at 190° C./5 Kg of 1 to 200 cm$^3$/10 minutes.

2. The process of claim 1 wherein said mole ratio of NCO groups to all active hydrogen atoms is 1:1.

3. The process of claim 1 wherein said 5-isocyanato-1-(isocyanatomethyl)-1,1,3-trimethylcyclohexane contains about 70 weight % of the cis isomer and about 30 weight % of the trans isomer.

4. The process of claim 1 wherein said bis-(4-isocyanatocyclohexyl)-methane contains 20 to 95 weight % of the trans,trans-isomer.

5. The process of claim 1 wherein said (B) is polytetrahydrofuran having a number average molecular weight of 1750 to 2500.

6. The process of claim 1 wherein said molar ratio (A):(B) is about 1.5:1 to 20:1.

7. The process of claim 1 wherein said molar ratio (A):(B) is about 2:1 to 12:1.

8. The process of claim 1 wherein (C.1) is isophorone diamine and said (C.2) is 1,6-hexanediol is the relative amounts of 50 to 30 mole % of (C.1) and 50 to 70 mole % of (C.2).

9. The process of claim 1 wherein said (D) is dibutylamine.

10. The process of claim 1 wherein said (D) is present in an amount of 2 to 6 equivalent %.

11. The polyurethane-urea elastomer produced by the process of claim 1.

12. An article of manufacture comprising the polyurethane-urea elastomer produced by the process of claim 1.

13. A process for the preparation of a polyurethane-urea elastomer having a mole ratio of NCO groups to all active hydrogen atoms in the range of 0.98 to 1.05 comprising reacting (A), (B) and (C.2) to form an NCO-containing prepolymer and then reacting said prepolymer with (C.1) and (D), where (A) is 5-isocyanato-1-(isocyanatomethyl)-1,1,3-trimethylcyclohexane, and where (B) is polytetrahydrofuran having a number average molecular weight of 1500 to 3000, and where the ratio of (A) to (B) is about 2:1 to 12:1 and where (C.2) is 1,6-hexanediol and (C.1) is 5-amino-3-aminomethyl-1,3,3-trimethylcyclohexane, and where the molar ratio of (C.1) to (C.2) is about 30 to 50 mole % of C.1 to 50 to 70 mole % of C.2, and where (D) is monoamine, present in an amount of 0.01 to 7 equivalent % based on the NCO groups included in (A), said process excluding a curing step, said elastomer characterized in having a melt volume index at 190° C./5 Kg of 1 to 200 cm$^3$/10 minutes.

14. A process for the preparation of a polyurethane-urea elastomer having a mole ratio of NCO groups to all active hydrogen atoms in the range of 0.98 to 1.2 comprising reacting (A), (B) and (C.2) to form an NCO-containing prepolymer and then reacting said prepolymer in an organic solvent with (C.1) and (D) where (A) is at least one member selected from the group consisting of 5-isocyanato-1-(isocyanatomethyl)-1,1,3-trimethylcyclo-hexane and bis-(4-isocyanatocyclohexyl)-methane and where B) is at least one member having a number average molecular weight of 1500 to 3000 selected from the group consisting of polytetrahydrofuran and hexanediol polycarbonate, and where the molar ratio (A):(B) is about 1.2:1 to 30:1, and where (C.2) is at least one member selected from the group consisting of 1,6-hexanediol, 1,4-butanediol, diethylene glycol, dipropylene glycol, tripropylene glycol and hydroquinone di-β-hydroxyethyl ether, and (C.1) is at least one member selected from the group consisting of 5-amino-3-aminomethyl-1,3,3-trimethylcyclohexane and bis-(4-amino-cyclohexyl)-methane and where the mole ratio (C.1):(C.2) is about 60:40 to 20:80, and where (D) is at least one molecular weight regulator selected from the group consisting of monoisocyanate, monoalcohol and monoamine present in an amount of 0.01 to 7 equivalent %, based on the NCO groups included in (A) said process excluding a curing step, said elastomer characterized in having a melt volume index at 190° C./5 Kg of 1 to 200 cm$^3$/10 minutes.

15. The process of claim 14 wherein said mole ratio of NCO groups to all active hydrogen atoms is 1:1.

16. The process of claim 14 wherein said 5-isocyanato-1-(isocyanatomethyl)-1,1,3-trimethylcyclohexane contains about 70 weight % of the cis isomer and about 30 weight % of the trans isomer.

17. The process of claim 14 wherein said bis-(4-isocyanato-cyclohexyl)-methane contains 20 to 95 weight % of the trans,trans-isomer.

18. The process of claim 14 wherein said (B) is polytetrahydrofuran having a number average molecular weight of 1750 to 2500.

19. The process of claim 14 wherein said molar ratio (A):(B) is about 1.5:1 to 20:1.

20. The process of claim 14 wherein said molar ratio (A):(B) is about 2:1 to 12:1.

21. The process of claim 14 wherein (C.1) is isophorone diamine and said (C.2) is 1,6-hexanediol is the relative amounts of 50 to 30 mole % of (C.1) and 50 to 70 mole % of (C.2).

22. The process of claim 14 wherein said (D) is dibutylamine.

23. The process of claim 14 wherein said (D) is present in an amount of 2 to 6 equivalent %.

24. The polyurethane-urea elastomer produced by the process of claim 14.

25. An article of manufacture comprising the polyurethane-urea elastomer produced by the process of claim 14.

* * * * *